(12) United States Patent
Hammonds et al.

(10) Patent No.: US 6,843,785 B2
(45) Date of Patent: Jan. 18, 2005

(54) SYSTEM AND METHOD FOR ATTACHING ABSORBENT ARTICLES

(75) Inventors: Yvette L. Hammonds, Oshkosh, WI (US); Shelley R. Rasmussen, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/037,277

(22) Filed: Dec. 20, 2001

(65) Prior Publication Data

US 2003/0036740 A1 Feb. 20, 2003

Related U.S. Application Data

(60) Provisional application No. 60/313,604, filed on Aug. 20, 2001.

(51) Int. Cl.$^7$ ............................. A61F 13/15; A61F 13/20
(52) U.S. Cl. ............................. 604/385.05; 604/385.04; 604/387; 604/391
(58) Field of Search .................. 604/385.04, 385.05, 604/387, 381, 385.18, 385.207; 24/442–452

(56) References Cited

U.S. PATENT DOCUMENTS

| | | | |
|---|---|---|---|
| 3,901,236 A | 8/1975 | Assarsson et al. | |
| 4,076,663 A | 2/1978 | Masuda et al. | |

(List continued on next page.)

FOREIGN PATENT DOCUMENTS

| | | |
|---|---|---|
| EP | 0 217 032 | 4/1987 |
| EP | 0 381 087 | 3/1994 |
| EP | 0 595 047 | 5/1994 |
| EP | 0 764 433 | 3/1997 |
| EP | 0 764 434 | 3/1997 |
| EP | 0 982 017 | 3/2000 |
| EP | 00/51540 | 9/2000 |
| WO | 98/15201 | 4/1998 |
| WO | 98/27903 | 7/1998 |
| WO | 99/55268 | 11/1999 |
| WO | 00/15069 | 3/2000 |
| WO | 00/72790 | 12/2000 |
| WO | 01/72254 | 10/2001 |

OTHER PUBLICATIONS

American Society for Testing Materials (ASTM) Designation: D 5169–91, "Standard Test Method for Shear Strength (Dynamic Method ) of Hook and Loop Touch Fasteners," pp. 687–689, published Nov. 1991.

American Society for Testing Materials (ASTM) Designation: D 5170–91, "Standard Test Method for Peel Strength ("T" Method) of Hook and Loop Touch Fasteners," pp. 690–692, published Nov. 1991.

Federal Test Method Standard (FTMS) No. 191A, Method 5514, "Water Resistance of Cloth; Low Range, Hydrostatic Pressure Method," Jul. 20, 1978, 3 pages.

TAPPI Official Test Method T 543 om–94, "Bending Resistance of Paper (Gurley Type Tester)," published by the TAPPI Press, Atlanta, Georgia, pp. 1–7.

Primary Examiner—Karin Reichle
(74) Attorney, Agent, or Firm—Ralph H. Dean, Jr.; Karl V. Sidor

(57) ABSTRACT

A system for attaching a personal care article to an undergarment, the system including: (a) providing a personal care article having a top surface, a bottom surface, garment attachment adhesive applied to the bottom surface, a peel strip covering the garment attachment adhesive and pair of wings including selectively releasable, interengaging fasteners such that the wings are adapted to be temporarily mechanically engaged on the topsheet side of the article and then reconfigured to hold the article to an undergarment; (b) overlapping and temporarily interengaging the wings on the top surface of the article while the peel strip protecting the garment adhesive is removed; (c) positioning the article in an undergarment and securing the article to the undergarment utilizing the garment adhesive; and (d) disengaging the wings and re-engaging the wings around the undergarment to further secure the article to the undergarment.

8 Claims, 8 Drawing Sheets

U.S. PATENT DOCUMENTS

| | | |
|---|---|---|
| 4,286,082 A | 8/1981 | Tsubakimoto et al. |
| 4,340,563 A | 7/1982 | Appel et al. |
| 4,608,047 A | 8/1986 | Mattingly |
| 4,663,220 A | 5/1987 | Wisneski et al. |
| 4,699,823 A | 10/1987 | Kellenberger et al. |
| 4,869,724 A * | 9/1989 | Scripps ............... 604/389 |
| 4,894,060 A | 1/1990 | Nestegard |
| 4,938,753 A | 7/1990 | Van Gompel et al. |
| 5,019,073 A | 5/1991 | Roessler et al. |
| 5,032,122 A * | 7/1991 | Noel et al. ............. 604/391 |
| 5,226,992 A | 7/1993 | Morman |
| 5,300,058 A | 4/1994 | Goulait et al. |
| 5,399,219 A | 3/1995 | Roessler et al. |
| 5,540,796 A | 7/1996 | Fries |
| 5,595,618 A | 1/1997 | Fries et al. |
| 5,605,735 A | 2/1997 | Zehner et al. |
| 5,624,429 A | 4/1997 | Long et al. |
| 5,676,652 A | 10/1997 | Hunter et al. |
| 5,704,929 A * | 1/1998 | Bien ............... 604/385.23 |
| 5,713,884 A | 2/1998 | Osborn, III et al. |
| 5,763,041 A | 6/1998 | Leak et al. |
| 5,782,819 A | 7/1998 | Tanzer et al. |
| 5,858,515 A | 1/1999 | Stokes et al. |
| 5,884,374 A | 3/1999 | Clune |
| 5,989,236 A | 11/1999 | Roe et al. |
| 6,030,373 A | 2/2000 | VanGompel et al. |
| 6,077,255 A | 6/2000 | Hunter et al. |
| 6,210,389 B1 | 4/2001 | Long et al. |
| 6,276,032 B1 | 8/2001 | Nortman et al. |
| 2003/0004484 A1 * | 1/2003 | Hammons et al. ..... 604/385.04 |
| 2003/0040730 A1 | 2/2003 | Hammonds et al. |
| 2003/0045856 A1 | 3/2003 | Couture et al. |
| 2003/0120251 A1 | 6/2003 | Couture et al. |

* cited by examiner

SYSTEM AND METHOD FOR ATTACHING ABSORBENT ARTICLES

This application claims the benefit of U.S. Provisional Application No. 60/313,604 entitled "MECHANICAL FASTENING SYSTEM HAVING ORTHOGONALLY ORIENTED ENGAGEMENT MEMBERS" and filed on Aug. 20, 2001, in the names of jason R. Cole, Denise R. Couture, Yvette L. Hammonds, Valerie R. Kurbec, Allan J. Krueger, Jason J. Manders, Shelley R. Rasmussen, David C. Strandberg, William G. Stratton, Manuel A. Torres, Jennifer A. Trottier, and Robert J. Waldron.

FIELD OF THE INVENTION

The present invention relates to fastening systems for garments and other articles. More particularly, the present invention relates to interlocking, mechanical-type fastening systems which can be employed with disposable personal care articles, such as sanitary napkins, incontinence pads and the like.

BACKGROUND

Absorbent articles such as sanitary napkins, incontinence pads and the like may be secured to an undergarment to hold the article in proper position during use. These articles frequently employ wings or flaps as well as garment attachment adhesive on the garment facing side of the article to secure the article to the undergarment. The wings or flaps typically employ adhesive to secure the end of the wing or flap to the undergarment.

Users often encounter difficulty attaching or applying the absorbent article. The peel strips or release materials covering the adhesive on the wings as well as the garment attachment adhesive are typically removed by the user at the same time. If the flexible wings contacts the garment attachment adhesive, the wings can get "stuck". Alternatively, the adhesive on the flexible wings may contact a portion of the article causing the wing to stick. In other situations, the adhesive on the flexible wings might stick together or the adhesive on the flexible wings might come into contact with the garment attachment adhesive. Each of these situations presents difficulties for the wearer to overcome when applying the article.

SUMMARY

The present invention addresses the problems discussed above by providing a system and method for attaching absorbent articles such as, for example, a sanitary napkin or an incontinence product to an undergarment.

According to the method of the invention, the fastening system provides ease of use or application benefits. In particular, flaps or wings of an article may be temporarily mechanically interengaged on the topsheet side or body side of the sanitary napkin or incontinence article while the peel strip protecting the garment adhesive is removed. The article may then be placed in position on an undergarment and then the wings may be engaged in a conventional manner.

The fastening system may include a personal care article having: a top surface defining a topsheet side, a bottom surface defining a backsheet side, garment attachment adhesive applied to the bottom surface, a peel strip covering the garment attachment adhesive as well as (A) a first wing extending from a first longitudinal edge of sanitary napkin and a second wing extending from a second longitudinal edge of the sanitary napkin, each wing having a fixed end and a free end; (B) selectively releasable, interengaging fasteners including: (i) a first fastener component forming at least a portion of the first wing and the second wing, the first fastener component including an engagement section having a plurality engagement members; and (ii) a cooperating fastener component forming at least a portion of the first wing and the second wing such that the wings are adapted to be temporarily mechanically engaged on the topsheet side of the article and then reconfigured to hold the article to an undergarment. The system further includes the following steps: overlapping and temporarily interengaging the wings on the top surface of the article while the peel strip protecting the garment adhesive is removed; positioning the article in an undergarment and securing the article to the undergarment utilizing the garment adhesive; and disengaging the wings and re-engaging the wings around the undergarment to further secure the article to the undergarment. In an embodiment of the invention, the fastening system may further include a fastener component including a plurality of engagement members configured so that it is adapted to engage a fabric undergarment positioned between the backsheet side and the wings.

Desirably, the fastening system includes:

(a) a first wing extending from a first longitudinal edge of the article (e.g., sanitary napkin) and a second wing extending from a second longitudinal edge of the article (e.g., sanitary napkin), each wing having a fixed end and a free end;

(b) a first fastener component that may form at least a portion of the first wing and the second wing, the first fastener component including an engagement section having a plurality engagement members; and (c) a cooperating fastener component that may form at least a portion of the first wing and the second wing such that the first and second wings of the article (e.g., sanitary napkin) are capable of being temporarily mechanically interengaged on the topsheet side or body side of the article (e.g., sanitary napkin) while a peel strip protecting the garment adhesive is removed. The article may then be placed in position on an undergarment and then the wings may be engaged in a conventional manner.

An aspect of the present invention is directed to a sanitary napkin having a pair of end edges, a first longitudinal edge and a second longitudinal edge located between the end edges, a backsheet layer, a substantially liquid permeable topsheet layer and an absorbent disposed between the topsheet layer and the backsheet layer. The sanitary napkin further incorporates a fastening system that includes:

(a) a first wing extending from a first longitudinal edge of sanitary napkin and a second wing extending from a second longitudinal edge of the sanitary napkin, each wing having a fixed end and a free end;

(b) a first fastener component that may form at least a portion of the first wing and the second wing, the first fastener component including an engagement section having a plurality engagement members; and (c) a cooperating fastener component that may form at least a portion of the first wing and the second wing such that the first and second wings of the sanitary napkin are capable of being temporarily mechanically interengaged on the topsheet side or body side of the sanitary napkin while a peel strip protecting the garment adhesive is removed. The sanitary napkin may then be placed in position on an undergarment and then the wings may be engaged in a conventional manner.

The first fastener component may have a plurality of substantially non-isotropic engagement members such that the engagement section has an axis of substantially maximal engagement and the first fastener component is oriented so its axis of substantially maximal engagement is generally orthogonal to the attachment direction. Each substantially non-isotropic engagement member may have a stem portion with a distal end region and a securement element disposed at the distal end region of its corresponding stem portion.

The cooperating fastener component can be a loop material such as, for example, a woven, knit and/or nonwoven loop material. As a further example, the nonwoven loop material an be a pattern unbonded material. For example, the nonwoven loop material may be a pattern unbonded material such as, for example, the material described in U.S. Pat. Nos. 5,858,515 and/or 5,763,041,the contents of which are incorporated herein by reference.

In as aspect of the invention, the fastening system can be used to secure the sanitary napkin or incontinence pad in a configuration convenient for disposal.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE INVENTION

Figure 1A:
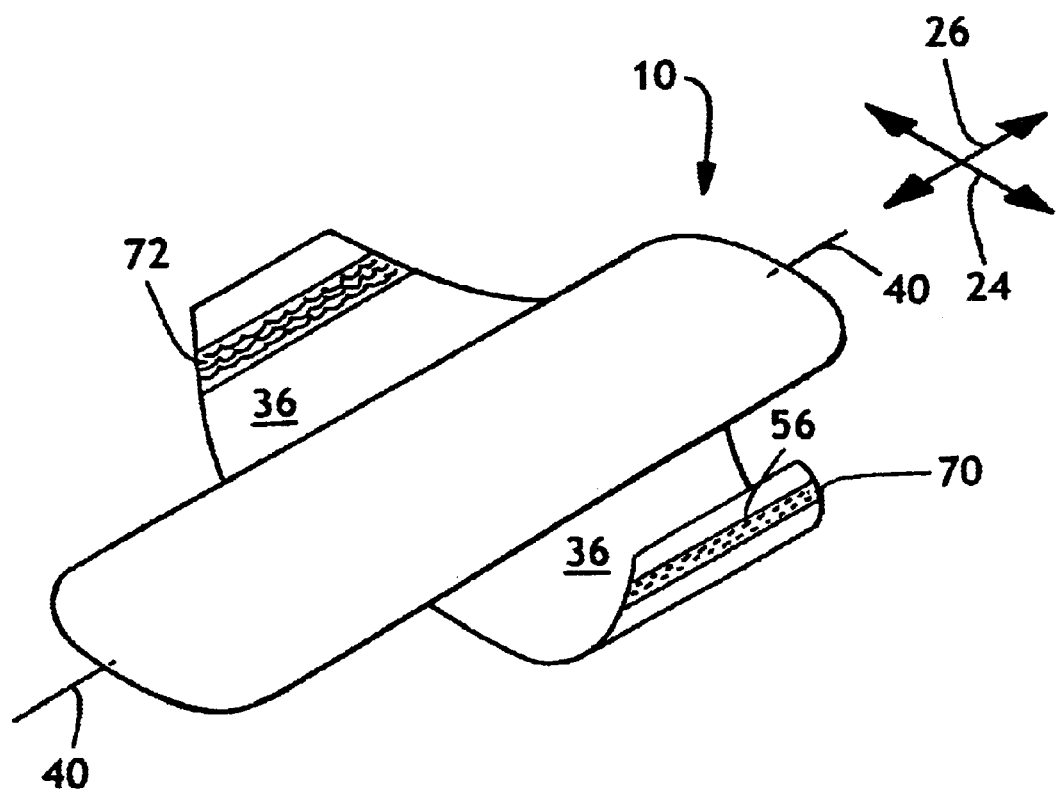
FIG. 1A is an illustration of an exemplary article incorporating an exemplary fastening system of the invention.
Figure 1B:
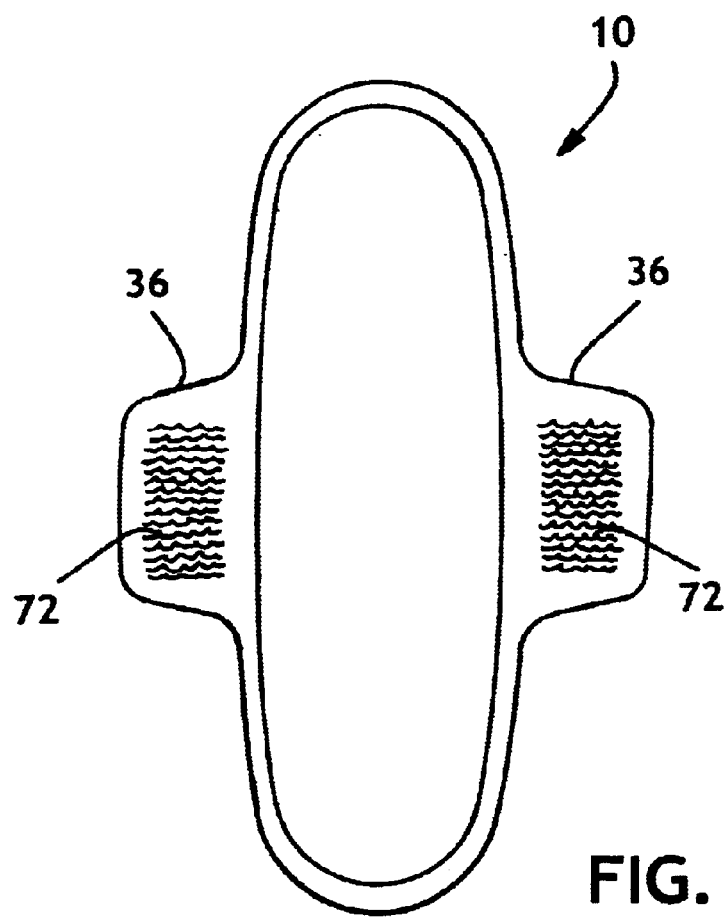
FIG. 1B is an illustration of an exemplary article incorporating an exemplary fastening system of the invention.

The various aspects and embodiments of the invention will be described in the context of a disposable absorbent article, such as a sanitary napkin or a disposable incontinence pad or the like. Typically, the disposable articles are intended for limited use and are not intended to be laundered or otherwise cleaned for reuse. A disposable sanitary napkin, for example, is discarded after it has become soiled by the wearer.

With reference to the Figures, an article, such as a sanitary napkin 10 illustrated in FIGS. 1A–E has a lengthwise, longitudinal direction 26, a lateral cross-direction 24, and a longitudinally extending medial line 40. The article includes a first article portion, a second article portion and at least one fastener 36 for securing the first article portion to the second article portion. Such securement can, for example, be configured to thereby hold the article on a wearer. The fastener desirably includes at least one, first fastener component 70 attached to an appointed section of the first (or second) article portion, and a cooperating fastener component 72 attached to the second (or first) particle portion. The first fastener component 70 includes an engagement section having a first plurality of engagement members 56. Each engagement member 56 has a stem portion with a distal end region, and has at least one securement element disposed at its corresponding distal end region. The plurality of engagement members has an arrangement pattern of their securement elements. It is contemplated that multiple pluralities of engagement members, each with different arrangement pattern of their securement elements, may be used.

Another aspect of the invention can provide an article in which the fastener component may include an engagement section having a plurality of non-isotropic engagement members. Each non-isotropic engagement member can have a stem portion with a distal end portion, and a direction-dependent securement element which is non-isotropically disposed at the distal end region of its corresponding stem portion to provide a non-isotropic engagement opening. The plurality of non-isotropic engagement members can have an alignment pattern of their engagement openings. It is contemplated that multiple pluralities of non-isotropic engagement members may be used and that different alignment patterns of their engagement openings are possible.

In particular configurations, a majority of the plurality of non-isotropic engagement members have their engagement openings directed substantially orthogonal to an attachment direction. Generally speaking, the attachment direction is the direction in which the respective first and second portions of the article are brought together into an overlapping and interengaging relationship. Thus, in FIGS. 1A–E the attachment direction is generally a direction having a cross-directional vector-component along the lateral direction 24 and toward the medial line 40 of the article. Accordingly, the plurality of non-isotropic engagement members would have their engagement openings directed substantially parallel with the medial line 40 of the article.

In the various aspects of the invention, the individual engagement members are typically flexible and resilient, but will substantially retain their initial shape during ordinary use. When flexed or deformed during ordinary use, the engagement members will substantially avoid plastically deforming to sustain the deformation, and will, instead, substantially return or "spring-back" to their original orientations and shape.

Figure 1C:
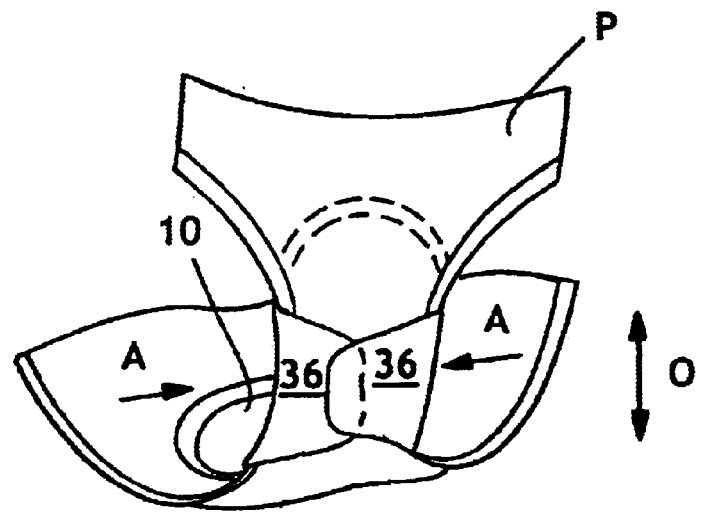
FIG. 1C is an illustration of an exemplary article incorporating an exemplary fastening system of the invention as it is used with an undergarment.

FIGS. 1A–1E are illustrations of an exemplary sanitary napkin with fasteners 36 in the form of wings or flaps. At least one first fastener component 70 is attached to the wing 36 and at least one cooperating fastener component 72 is attached to the opposite wing 36. In some embodiments of the invention, the first fastener component 70 and the cooperating fastener component 72 may be attached to each wing such that the wings may be fastened without concern for overlapping the wings in any particular order. In other yet embodiments, the wing may be formed partially or entirely of the cooperating fastener component 72 as shown by, for example, FIGS. 1B, 1D, 1D' and 1E. FIG. 1C is an illustration of the sanitary napkin with its wings 36 or flaps secured around an undergarment or panty P. The arrows labeled A generally represent the attachment direction. The arrows labeled O generally represent the direction that is orthogonal to the attachment direction. It should be understood that this orthogonal direction is thought to be generally or substantially along or in the plane of the article although in some specific cases, it includes a minor Z-direction component.

According to the invention, the first fastener component should be configured to have an axis of maximal engagement. This can be accomplished by utilizing a plurality of engagement members 56 that are non-isotropic (i.e., anisotropic) or non-symmetric. When the axis of maximal engagement of the first fastener component is oriented to be generally orthogonal to the attachment direction (that is, the direction each fastener component is generally brought together to effect overlapping engagement), it has been unexpectedly found that the fastening system is adapted to become more interengaged as the product is worn. For example, peel force and shear force as determined utilizing standard test procedures prior to wearing the article is greater for fastening systems in which the axis of maximal engagement of the first fastener component is oriented in the attachment direction and lower for fastening systems in which the axis of maximal engagement of the first fastener component is oriented orthogonal to the attachment direction.

When the peel force and the shear force were measured after use, the values increased for both orientations. However, the peel force and sheer force values measured for fastening systems in which the axis of maximal engagement of the first fastener component is oriented orthogonal to the attachment direction were greater than those measured for fastening systems in which the axis of maximal engagement of the first fastener component is oriented in the attachment direction.

Figure 1D:
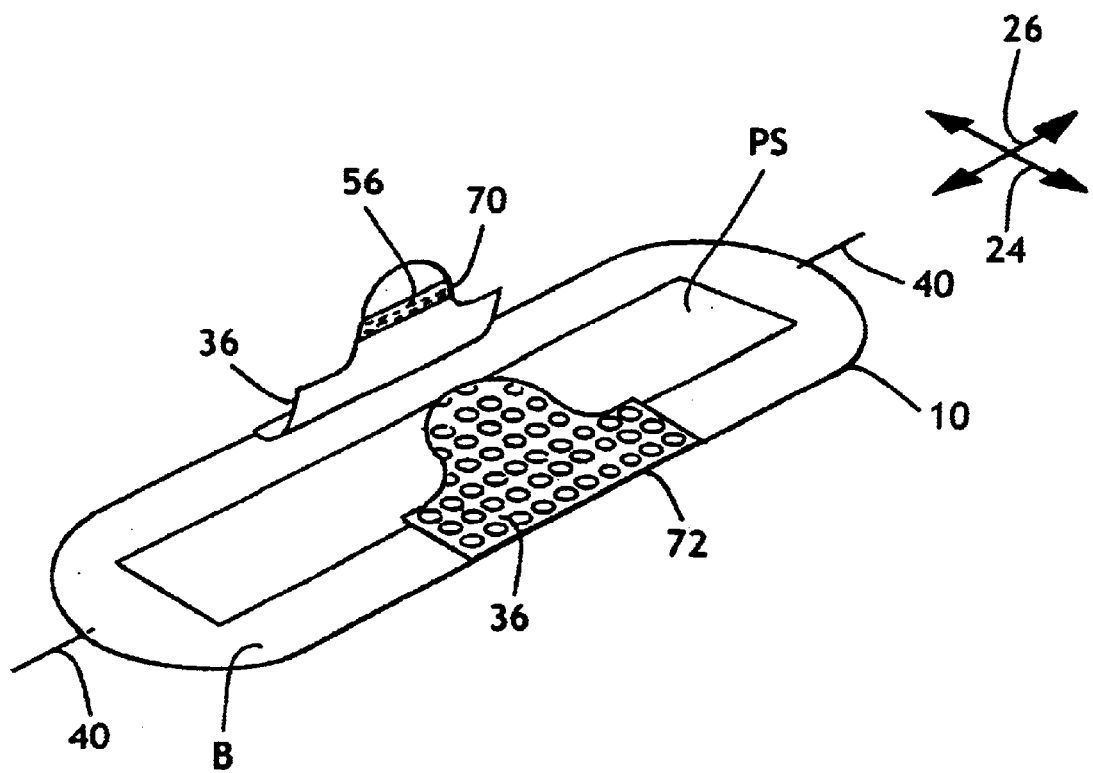
FIG. 1D is an illustration of an exemplary article incorporating an exemplary fastening system of the invention— with the backsheet of the article facing upward.
Figure 1D:
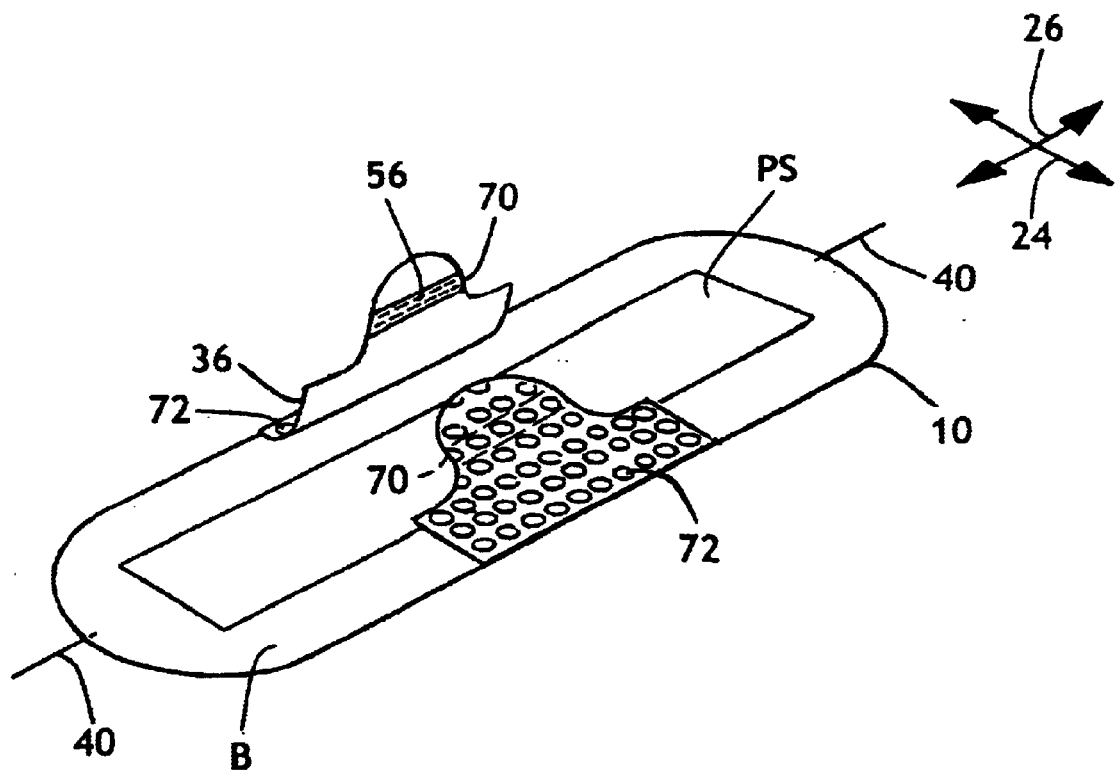
Figure 1E:
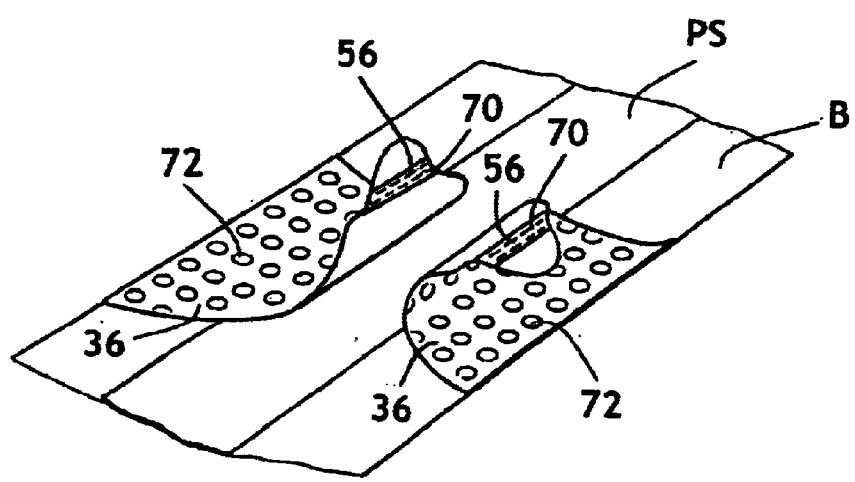
FIG. 1E is an illustration of a portion of an exemplary article incorporating an exemplary fastening system of the invention—with the backsheet of the article facing upward.

The following is a brief description of the orientation direction with respect to the lengthwise, longitudinal direction 26 and the lateral cross-wise direction depicted in FIGS. 1A, 1D and 1D'. In one exemplary sanitary napkin, the orientation of the axis of maximal engagement of the first fastener component in the attachment direction meant orienting the first fastener component so its axis of maximal engagement was in the cross-machine direction or the lateral cross-direction 24 shown in FIGS. 1A, 1D and 1D'. Thus, for that sanitary napkin, the orientation of the axis of maximal engagement of the first fastener component generally orthogonal to the attachment direction meant orienting the first fastener component so its axis of maximal engagement was in the machine direction or the lengthwise, longitudinal direction 26 shown in FIGS. 1A, 1D and 1D'.

Figure 5A:
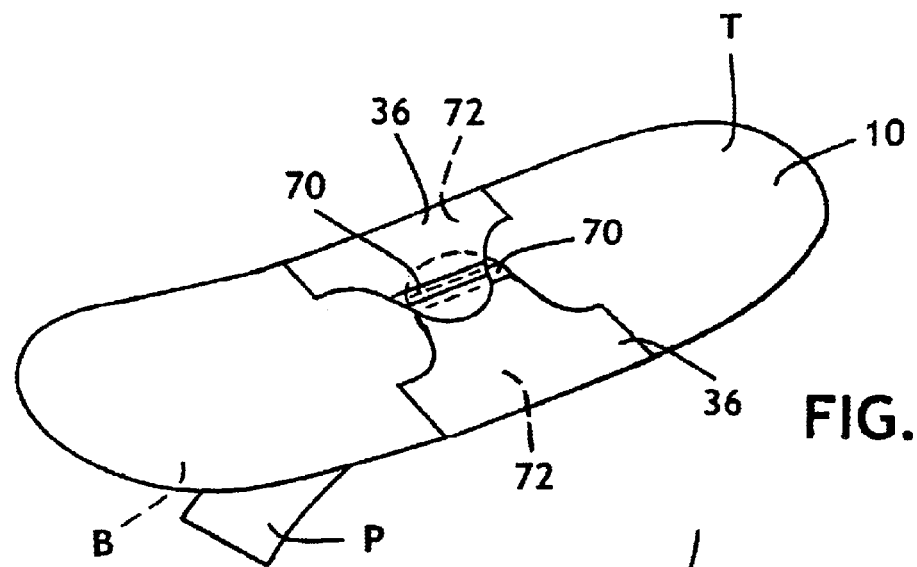
FIGS. 5 A–C are illustrations of a sequence showing an exemplary method of the present invention when applying an article that employs the fastening system of the present invention.
Figure 5B:
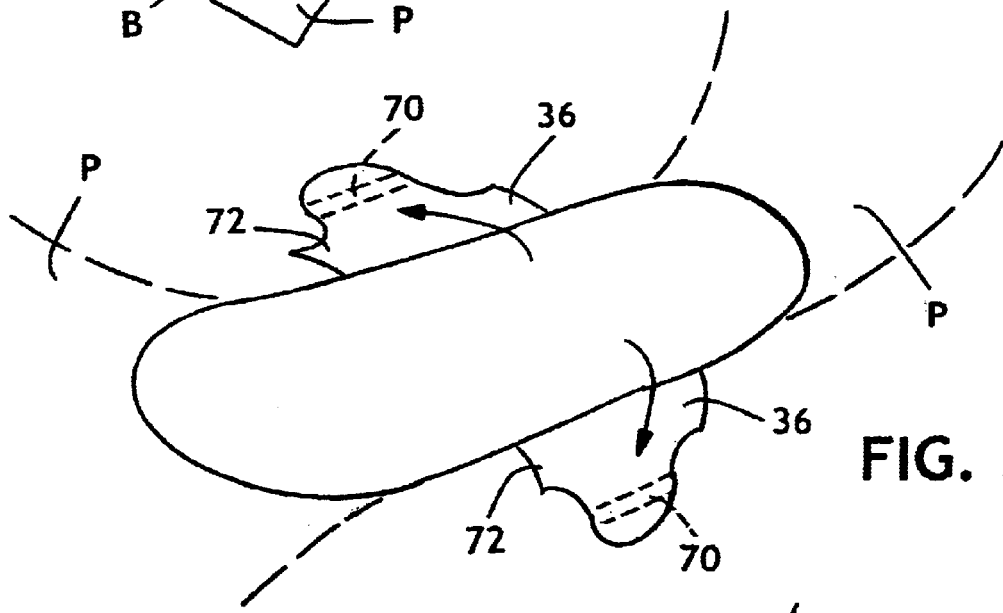
Figure 5C:
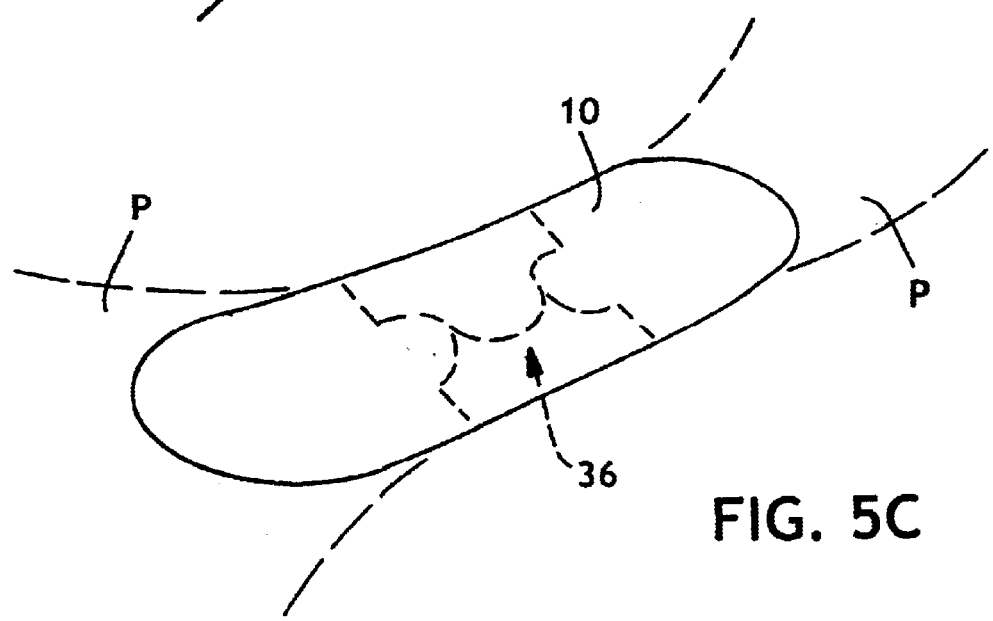

In another aspect of the invention, the fastening system also provides ease of use or application benefits. As shown in FIGS 5A–C, the wings or fasteners 36 may be engaged on the topsheet side T or body side of the sanitary napkin or incontinence article 10 while the peel strip PS protecting the garment adhesive (not shown) is removed. The article may then be placed in position on an undergarment P then the wings may be engaged.

The present invention also encompasses a sanitary napkin or incontinence pad that has an attachment system having wings that are adapted to hold, secure, attach or join the sanitary napkin or incontinence pad to an undergarment as well as a fastener component including a plurality of engagement members that are adapted to engage the fabric of an undergarment to also help hold, secure, attach or join the sanitary napkin or incontinence pad to the undergarment. In particular, FIG. 5A shows such a system in which the fasteners or wings 36 that may be formed of the cooperating fastener component 72 are engaged by contact with the first fastener component 70. A strip of garment adhesive (not shown) on the backsheet side or garment side B of the article 10 can help secure the article to the underwear P. In addition, a first fastener component 70 is in a position to engage the fabric of the underwear P while the fasteners or wings 36 secure or join the article to the underwear P by wrapping around the underwear.

With reference to the representative configurations shown in FIGS. 1A–E, the article can include a system of flap regions, wings, "ear" regions or ear members. In particular arrangements, each flap, wing or ear region or member may extend laterally at the opposed, lateral ends of the article such as an incontinence pad or sanitary napkin.

In the various configurations of the invention, the ear, tab, flap or wing regions may be integrally formed with a selected article component. For example, ear, tab, flap or wing regions can be integrally formed from the layer of material which provides backsheet layer and/or may be integrally formed from the material employed to provide topsheet. In alternative configurations, the ear, tab, flap or wing regions may be provided by one or more separately provided members that are connected and assembled to the backsheet, to the topsheet, in between the backsheet and topsheet, or in various fixedly attached combinations of such assemblies.

In particular configurations of the invention, each of the ear, tab, flap or wing regions may be formed from a separately provided piece of material which is then suitably assembled and attached to a selected portion of the article.

The ear, tab, flap or wing regions may be composed of a substantially non-elastomeric material, such as polymer films, woven fabrics, nonwoven fabrics or the like, as well as combinations thereof. In particular aspects of the invention, ear, tab, flap or wing regions may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24. For example, suitable meltblown elastomeric fibrous webs for forming ear, tab, flap or wing regions are described in U.S. Pat. No. 4,663,220 issued May 5, 1987 to T. Wisneski et al., the entire disclosure of which is hereby incorporated by reference. Examples of composite fabrics comprising at least one layer of nonwoven textile fabric secured to a fibrous elastic layer are described in European Patent Application EP 0 217 032 A2 published on Apr. 8, 1987 which has the listed inventors of J. Taylor et al., the entire disclosure of which is hereby incorporated by reference. Examples of NBL materials are described in U.S. Pat. No. 5,226,992 issued Jul. 13, 1993 to Mormon, the entire disclosure of which is hereby incorporated by reference in a manner that is consistent herewith.

As previously mentioned, various suitable constructions can be employed to attach the ear, tab, flap or wing regions to the selected portions of the article. Particular examples of suitable constructions for securing a pair of elastically stretchable members to the lateral, side portions of an article to extend laterally outward beyond the laterally opposed side regions of the outer cover and liner components of an article can be found in U.S. Pat. No. 4,938,753 issued Jul. 3, 1990 to P. VanGompel et al., the entire disclosure of which is hereby incorporated by reference in a manner that is consistent herewith.

The illustrated ear, tab, flap or wing regions have a tapered, curved or otherwise contoured shape in which the longitudinal length of the relatively inboard base region is larger or smaller than the longitudinal length of its relatively outboard end region. Alternatively, the ear regions may have a substantially rectangular shape, and optionally may have a substantially trapezoidal shape.

In the various aspects and configurations of the invention, the fastening mechanism between the selected first fastener component and the selected, cooperating fastener component may be adhesive, cohesive, mechanical or combinations thereof. In the context of the present invention, a mechanical fastening system is a system which includes a first fastener component and cooperating fastener component which mechanically inter-engage to provide a desired securement.

Desirably, the first fastener component and cooperating fastener components include complementary elements of a cooperatively interengaging mechanical fastening system. The mechanical fastener components can be provided by mechanical-type fasteners such as hooks, buckles, snaps, buttons and the like, which include cooperating and complementary, mechanically interlocking components.

As shown in the illustrated arrangements, for example, the mechanical fastening system may be a hook-and-loop type of fastening system. Such fastening systems typically include engagement members having the form of a "hook" or hook-like, male component, and include a cooperating "loop" or loop-like, female component which engages and releasably interconnects with the hook component. Desirably, the interconnection is selectively releasable and re-attachable. Conventional systems are, for example, available under the VELCRO trademark. The hook element may be provided by a single-prong hook configuration, a multiple-prong hook configuration or by a generally continuous, expanded-head configuration, such as provided by a mushroom-head type of hook element. The loop element may be provided by a woven fabric, a nonwoven fabric, a knitted fabric, a perforated or apertured layer, and the like, as well as combinations thereof. The many arrangements and variations of such fastener systems have been collectively referred to as hook-and-loop fasteners.

A configuration which employs a selectively releasable, interengaging mechanical fastening system can, for example, locate the first fastener component on at least the appointed mating or securing surface of the tab, flap or wing 36, and can locate the cooperating fastener component on the appointed engagement surface of the appointed tab, flap or wing 36. For example, with the representatively shown hook-and-loop fastener, the fastening component which is attached to the appointed mating or securing surface of a fastener tab 36 may include a hook type of mechanical engagement element, and the complementary fastening component, which is operably joined and attached to the appointed surface of a fastener tab 36 can include a loop type of fastening element.

It should also be readily apparent that, in the various configurations of the invention, the relative positions and/or materials of the first fastening component and its cooperating, complementary fastening component can be transposed.

Examples of hook-and-loop fastening systems and components are described in U.S. Pat. No. 5,019,073 issued May 28, 1991 to T. Roessler et al., the entire disclosure of which is hereby incorporated by reference in a manner that is consistent herewith. Other examples of hook-and-loop fastening systems are described in U.S. patent application Ser. No. 366,080 entitled HIGH-PEEL TAB FASTENER, filed Dec. 28, 1994 by G. Zehner et al. which corresponds to U.S. Pat. No. 5,605,735; and U.S. patent application Ser. No. 421,640 entitled MULTI-ATTACHMENT FASTENING SYSTEM, filed Apr. 13, 1995 by P. VanGompel et al.; the entire disclosures of which are hereby incorporated by reference in a manner that is consistent herewith. Examples of fastening tabs constructed with a carrier layer are described in U.S. patent application Ser. No. 08/603,477 of A. Long et al., entitled MECHANICAL FASTENING SYSTEM WITH GRIP TAB and filed Mar. 6, 1996 which corresponds to U.S. Pat. No. 5,624,429 which issued Apr. 29, 1997, the entire disclosure of which is hereby incorporated by reference in a manner which is consistent herewith.

Figure 2A:
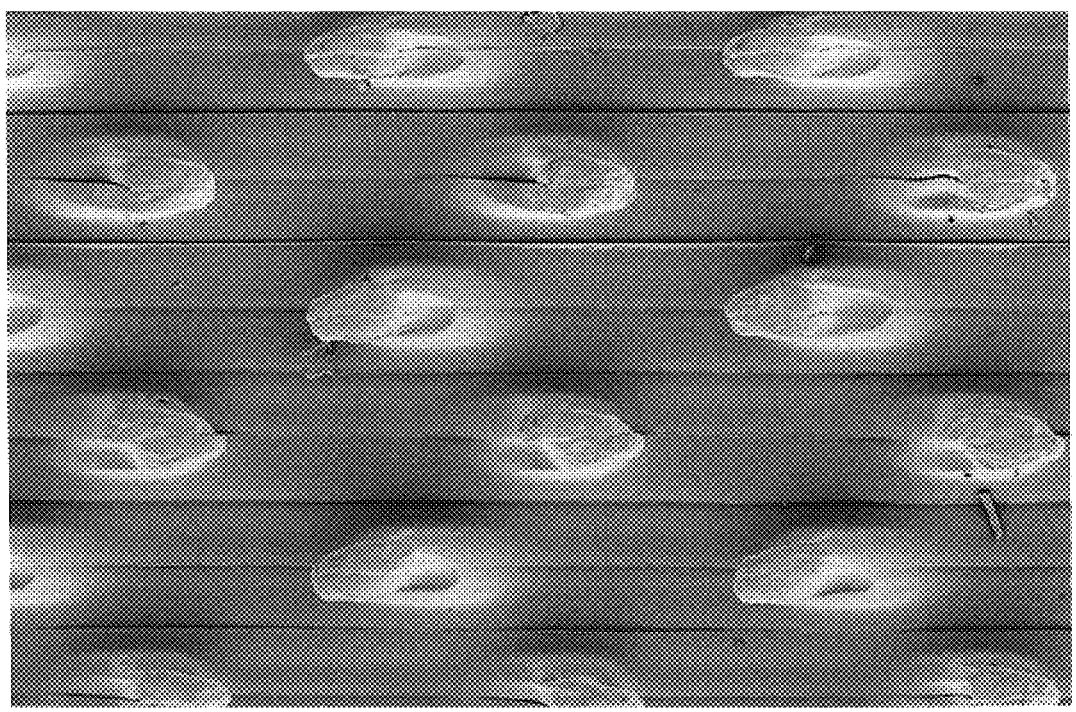
FIGS. 2A–B are photomicrographs of an exemplary, non-isotropic engagement member which can be employed with the present invention.
Figure 2B:
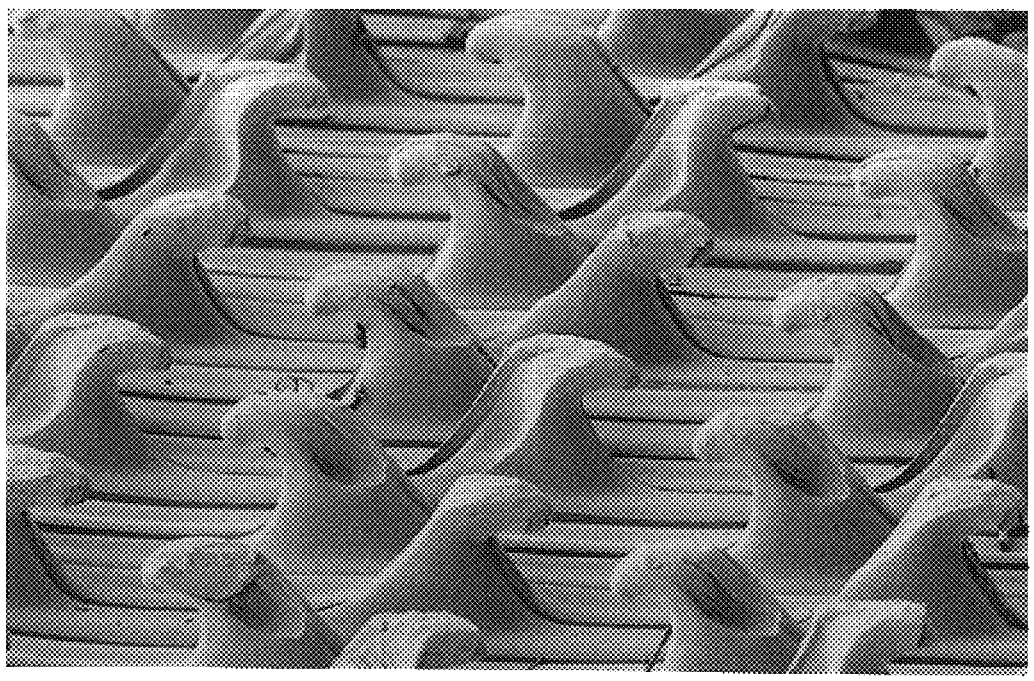

An example of a suitable micro-hook material is distributed under the designations VELCRO HTH 829 and VELCRO HTH 851 and is available from VELCRO U.S.A., Inc., a business having offices in Manchester, N.H. VELCRO HTH 851 micro-hook material is shown in photomicrographs in FIGS. 2A and 2B. FIG. 2A is top view (linear magnification of 45x) of the micro-hook material shown in an example of the relative distribution of individual engagement members or elements. FIG. 2B is a perspective view (linear magnification of 50x) showing an example of the angled engagement members or hook elements. The micro-hook material can have hooks in the shape of angled hook elements, and can be configured with a hook density of about 264 hooks per square centimeter (about 1700 hooks per square inch); a hook height which is within the range of about 0.030–0.063 cm (about 0.012–0.025 inch); and a hook width which is within the range of about 0.007 to 0.022 cm (about 0.003 to 0.009 inch). The hook elements are molded onto a base layer substrate having a thickness of about 0.0076–0.008 cm (about 0.003–0.0035 inch), and the member of hook material has a Gurley stiffness of about 12 mgf (about 12 Gurley units). Other suitable hook materials can include VELCRO HTH 858 and VELCRO HTH 863 hook materials.

For the purposes of the present invention, the various stiffness values are determined with respect to a bending moment produced by a force which is directed perpendicular to the plane substantially defined by the length and width of the component being tested. A suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester; Model 4171-D manufactured by Teledyne Gurley, a business having offices in Troy, N.Y. For purposes of the present description, the stated Gurley stiffness values are intended to correspond to the values that would be generated by a "standard" sized sample. Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness.

Figure 3:
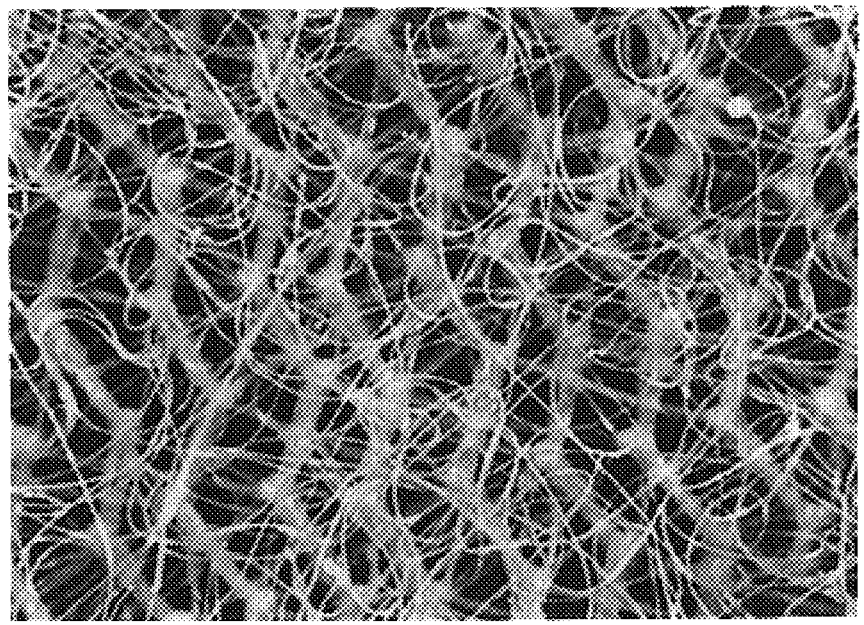
FIGS. 3 and 4 are photomicrographs of exemplary cooperating fastener members (e.g., loop materials) that may be used with the present invention.

In the various aspects and configurations of the invention, the loop material can be provided by a nonwoven, woven or knit fabric. For example, a suitable loop material fabric can be composed of a 2 bar, warp knit fabric of the type available from Guilford Mills, Inc., Greensboro, N.C. under the trade designation #34285, as well as other types of knit fabrics. FIG. 3 is a photomicrograph depicting an exemplary cooperating fastener member in the form of the loop material fabric available from Guilford Mills. Inc. Suitable loop materials are also available from the 3M Company, which has distributed a nylon woven loop under their SCOTCH-MATE brand. The 3M Company has also distributed a linerless loop web with adhesive on the backside of the web, and 3M knitted loop tape.

Figure 4:
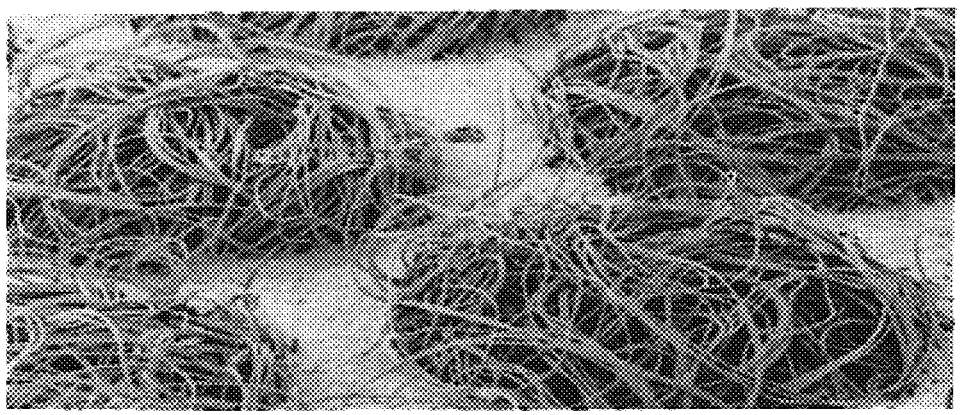

The loop material may also include a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web may include a spunbond nonwoven web formed of single component or multi-component melt-spun filaments. At least one surface of the nonwoven fabric can include a plurality of discrete, unbonded areas surrounded or encircled by continuous bonded areas. The continuous bonded areas dimensionally stabilize the fibers or filaments forming the nonwoven web by bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web non-fibrous within the bonded areas, leaving the fibers or filaments within the unbonded areas to act as "loops" for receiving and engaging hook elements. Examples of suitable point-unbonded fabrics are described in U.S. Pat. No. 5,858,515 entitled PATTERN UNBONDED NONWOVEN WEB AND PROCESS FOR MAKING THE SAME, by T. J. Stokes et al., the entire disclosure of which is incorporated herein by reference in a manner that is consistent herewith. FIG. 4 is a photomicrograph (linear magnification 17×) depicting an exemplary cooperating fastener member in the form of a pattern unbonded nonwoven web generally as described in U.S. Pat. No. 5,858,515. As is evident from the photomicrographs, a plurality of discrete, unbonded areas that are adapted to engage the engagement members are surrounded or encircled by continuous bonded areas.

In the various configurations of the invention, the loop material need not be limited to a discrete or isolated patch on the outward surface of the article. Instead, the loop material can be provided by a substantially continuous, outer fibrous layer which is assembled, integrated or otherwise joined to extend over a predetermined surface area of the desired article. For example, the outer fibrous layer may be arranged to extend over substantially the total exposed surface area of a cloth-like outer cover employed with the article.

In the various configurations of the invention, the engagement force between the selected first fastener component and its appointed and cooperating fastener component should be large enough and durable enough to provide an adequate securement of the article on the wearer during use. In particular arrangements, especially where there are sufficiently high levels of engagement shear force provided by the fastening system, the fastening engagement may provide a peel force value of not less M than a minimum of about 40 grams-force (gmf) per inch of the "width" of engagement between the first and cooperating fastener components. In further arrangements, the fastening engagement may provide a peel force value of not less than about 100 gmf/inch to provide improved advantages. In desired configurations, the fastening engagement may provide a peel force value of not less than about 200 gmf per inch of the "width" of engagement between the first and cooperating fastener components. Alternatively, the peel force is not less than about 300 gmf/inch, and optionally is not less than about 400 gmf/inch to further provide improved benefits. In other aspects, the peel force is not more than about 1,200 gmf/inch. Alternatively, the peel force is not more than about 800 gmf/inch, and optionally is not more than about 600 gmf/inch to provide improved performance.

The engagement force between the selected first fastener component and its appointed and cooperating fastener component may additionally provide a shear force value of not less than about 400 gmf per square inch of the area of engagement between the first and second fastener components. Alternatively, the shear force is not less than about 1,000 gmf/inch$^2$, and optionally, is not less than about 1,700 gmf/in$^2$. In further aspects, the shear force can be up to about 4,400 gmf/in$^2$, or more. Alternatively, the shear force is not more than about 3,900 gmf/in$^2$, and optionally is not more than about 3,500 gmf/in$^2$ to provide improved performance.

The peel force value can be determined in accordance with standard procedure ASTM D-5170, approved Sep. 15, 1991 and published November 1991; with the following particulars. The test specimen is the fastener tab from the article being assessed. The test specimen length is the dimension aligned along the direction in which a peel-away force is typically applied to disengage and remove the fastener during the ordinary use of the article with which the fastener is employed. The specimen "width" lies within the general plane of the fastener and is perpendicular to the specimen length. The roller device weighs 4.5 pounds and includes a rubber coating around the roller circumference. A suitable roller is part number HR-100 available from Chemsultants International, a business having a location in Mentor, Ohio. During the engagement of the fastener components, the roller is rolled over the test specimen through one cycle in the direction of the cross-wise "width" of the sample. In addition, the initial peel by hand to "raise the loops" is omitted. During testing, the fastener material held by the stationary clamp can be larger in area, as compared to the fastener material held in the moving clamp. The initial separation distance between the clamps of the tensile tester is 4 inch, and the extension speed of the tensile testing machine is 20 inch/min. The reported value of a peel test result is a "three-peak average" value employing MTS TESTWORKS software with a peak criteria of 2%. Additionally, the peel force value is normalized to be stated in terms of force per unit length of the "width" dimension of the fastener component on the test specimen, such as grams per inch. The MTS TESTWORKS software is available from MTS Systems Corporation, a business having offices in Eden Prairie, Minn.

The shear force value can be determined in accordance with the standard procedure ASTM D-5169, approved Sep. 15, 1991 and published November 1991 with the following particulars. The test specimen is composed of the fastener tab from the article being assessed. The test specimen length and width typically correspond to the length and width employed to conduct the testing for peel force value. Ordinarily, the test specimen length is the dimension aligned along the direction in which a shear force is typically applied to the fastener during the ordinary use of the article with which the fastener is employed. The specimen "width" lies within the general plane of the fastener and is perpendicular to the specimen length. The roller device weighs 4.5 pounds and includes a rubber coating around the roller. A suitable roller is part number HR-100 available from Chemsultants International, a business having a location in Mentor, Ohio. During the engagement of the fastener components, the roller is rolled over the test specimen through five cycles in the direction of the cross-wise "width" of the sample. In addition, the initial peel by hand to "raise the loops" is omitted. During testing, the fastener material (e.g. the loop material) held by the stationary clamp can be larger in area, as compared to the fastener material (e.g. hook material) held in the moving clamp. The initial separation distance between the clamps of the tensile tester is 4 inch, and the extension speed of the tensile testing machine is 10 inch/min. The shear force value is normalized to be stated in terms of force per unit area of the test specimen, such as grams per inch$^2$.

The particulars of the standard test procedures are intended to generate fastening conditions that can be more representative of consumer use conditions. When preparing the test specimen materials (e.g. hook and loop materials) to determine the cooperating peel and/or shear force values for the representatively shown configurations of the invention, it should be noted that, the width dimension of the selected specimen material will correspond to the dimension of the fastener material which, in the actual article, is found to be aligned along the longitudinal direction 26 of the article. Similarly, the length dimension of the selected specimen material will correspond to the dimension of the fastener material which, in the actual article, is found to be aligned along the lateral direction 24 of the article.

Desirably, the securing engagement between the first fastener component and the cooperating fastener components should be sufficient to prevent a disengagement of the components when subject to a tensile force of at least about 1,000 grams when the tensile force is applied outwardly along the lateral direction, aligned generally parallel with the plane of the backsheet layer of the article.

Each of the fastener components and fastening elements in the various constructions of the invention may be operably attached to its supporting substrate by employing any one or more of the attachment mechanisms employed to construct and hold together the various other components of the article of the invention. The fastening elements in the various fastening regions, may be integrally formed, such as by molding, co-extrusion or the like, along with their associated substrate layer. The substrate layer and its associated mechanical fastening elements may be formed from substantially the same polymer material, and there need not be a discrete step of attaching the fastening elements to an initially separate substrate layer. For example, the individual hook elements may be integrally formed simultaneously with a hook base-layer by coextruding the base layer and hook elements from substantially the same polymer material.

It should be readily appreciated that the strength of the attachment or other interconnection between the substrate layer and the attached fastening component should be greater than the peak force required to remove the fastener tab 36 from its releasable securement to the appointed landing member of the article.

Having described the invention in rather full detail, it will be readily apparent that various changes and modifications can be made without departing from the spirit of the invention.

We claim:

1. A method for securing a personal care article to a fabric undergarment, the method comprising;

providing a personal care article comprising:
 a top surface defining a topsheet side,
 a bottom surface defining a backsheet side,
 a garment attachment adhesive applied to the bottom surface,
 a peel strip covering the garment attachment adhesive,
 a first wing extending from a first longitudinal edge of the personal care article and a second wing extending from a second longitudinal edge of the personal care article, each wing having a fixed end, a free end, a top surface and a bottom surface; and
 selectively releasable, interengaging fasteners including: (i) a first fastener component forming at least a portion of one of the surfaces of the first wing and at least a portion of one of the surfaces of the second wing generally adjacent the free end of each wing, each first fastener component including an engagement section having a plurality of engagement members; and (ii) a cooperating fastener component forming at least a portion of the other surface of the first wing and at least a portion of the other surface of the second wing generally adjacent the free end of each wing, both the one surface of the first wing and the one surface of the second wing being either the top surface or the bottom surface; such that the wings are adapted to be temporarily mechanically engaged on the topsheet side of the article and then reconfigured to hold the article to the undergarment;

overlapping and temporarily interengaging the first fastener component of one wing and the cooperating fastener of the other wing on the top surface of the personal care article;

removing the peel strip protecting the garment adhesive;

positioning the article in the undergarment and securing the article to the undergarment utilizing the garment adhesive; and disengaging the temporarily overlapped wings on the top surface and re-engaging the first fastener component of the one wing and the cooperating fastener of the other wing after the wings are wrapped around the undergarment to further secure the article to the undergarment for use.

2. The method of claim 1, wherein the step of providing the personal care article comprises providing a sanitary napkin.

3. The method of claim 1, wherein the step of re-engaging the first fastener component further comprises the step of positioning the first fastener component on the other wing adjacent the bottom surface of the personal care article adjacent the fabric of the undergarment and engaging the first fastener component on the other wing adjacent the fabric of the undergarment with the fabric of the undergarment.

4. The method of claim 3, wherein the step of providing the personal care article comprises providing a sanitary napkin.

5. The method of claim 1, further comprising the step of providing each first fastener component in the form of a mechanical hook material and each cooperating fastener component in the form of a loop material.

6. The method of claim 5, wherein the step of providing the personal care article comprises providing a sanitary napkin.

7. The method of claim 1, further comprising the steps of disengaging the wings after use and utilizing the selectively releasable interengaging fasteners to secure the article in a configuration convenient for disposal.

8. The method of claim 7, wherein the step of providing the personal care article comprises providing a sanitary napkin.

* * * * *